US009376734B2

(12) United States Patent
Goto et al.

(10) Patent No.: US 9,376,734 B2
(45) Date of Patent: Jun. 28, 2016

(54) INDIUM EXTRACTION AGENT AND INDIUM EXTRACTION METHOD (71) Applicants: Kyushu University, National University Corporation, Fukuoka-Shi (JP); SUMITOMO METAL MINING CO., LTD., Tokyo (JP)

(72) Inventors: Masahiro Goto, Fukuoka (JP); Fukiko Kubota, Fukuoka (JP); Yuzo Baba, Fukuoka (JP)

(73) Assignees: Kyushu University, National University Corporation, Fukuoka-shi (JP); SUMITOMO METAL MINING CO., LTD., Tokyo (JP)

( * ) Notice: Subject to any disclaimer, the term of this patent is extended or adjusted under 35 U.S.C. 154(b) by 0 days.

(21) Appl. No.: 14/423,093

(22) PCT Filed: Apr. 26, 2013

(86) PCT No.: PCT/JP2013/062480
§ 371 (c)(1),
(2) Date: Feb. 20, 2015

(87) PCT Pub. No.: WO2014/030394
PCT Pub. Date: Feb. 27, 2014

(65) Prior Publication Data
US 2015/0259768 A1 Sep. 17, 2015

(30) Foreign Application Priority Data

Aug. 20, 2012 (JP) ................................. 2012-181884

(51) Int. Cl.
*C22B 58/00* (2006.01)
*C22B 3/00* (2006.01)
(Continued)

(52) U.S. Cl.
CPC ............ *C22B 58/00* (2013.01); *B01D 11/0492* (2013.01); *C07C 237/06* (2013.01);
(Continued)

(58) Field of Classification Search
CPC ............. B01D 11/0492; C07D 233/64; C07C 237/06; C22B 3/032; C22B 58/00; C22B 3/0032
See application file for complete search history.

(56) References Cited

U.S. PATENT DOCUMENTS 5,326,760 A * 7/1994 McElroy et al. ........... 514/235.2
8,951,486 B2 2/2015 Goto et al.
(Continued)

FOREIGN PATENT DOCUMENTS

CN 103582711 2/2014
JP 2000-212658 A 8/2000
(Continued)

OTHER PUBLICATIONS

Pajewski, Robert et al. "The Effect of Midpolar Regime Mimics on Anion Transport Mediated by Amphiphilic Heptapeptides." New Journal of Chemistry, 2007 (31) pp. 1960-1972.*
(Continued)

*Primary Examiner* — George Wyszomierski
*Assistant Examiner* — Tima McGuthry-Banks
(74) *Attorney, Agent, or Firm* — Locke Lord LLP (57) ABSTRACT Provided are an extraction agent and extraction method that selectively extract and, at a low cost, recover indium from an acidic solution containing indium and zinc. The indium extraction agent comprises an amide derivative represented by general formula (I). In the formula, $R^1$ and $R^2$ each indicate the same or different alkyl group, $R^3$ indicates a hydrogen atom or an alkyl group, and $R^4$ indicates a hydrogen atom or any given group, other than an amino group, bound to the α-carbon as an amino acid. The general formula preferably has a glycine unit, a histidine unit, a lysine unit, an aspartic acid unit, or an N-methylglycine unit. By extracting indium from an acidic solution containing indium and zinc by means of solvent extraction using the extraction agent, it is possible to selectively extract indium.

16 Claims, 6 Drawing Sheets (51) Int. Cl.
  *C07D 233/64*   (2006.01)
  *C07D 237/06*   (2006.01)
  *B01D 11/04*    (2006.01)
  *C07C 237/06*   (2006.01)
  *C22B 3/26*     (2006.01)
  *C22B 3/32*     (2006.01)
  *C22B 3/38*     (2006.01)

(52) U.S. Cl.
  CPC .............. *C07D233/64* (2013.01); *C22B 3/005* (2013.01); *C22B 3/0024* (2013.01); *C22B 3/0032* (2013.01); *Y02P 10/234* (2015.11); *Y02P 20/582* (2015.11)

(56) References Cited

U.S. PATENT DOCUMENTS

2007/0172404 A1   7/2007   Narita et al.
2014/0234187 A1   8/2014   Goto et al.

FOREIGN PATENT DOCUMENTS

JP    2007-327085 A    12/2007
JP    2009256291 A     11/2009
JP    2012-102062 A    5/2012
WO    WO-2005-083131 A1   9/2005

OTHER PUBLICATIONS

Hirofumi Morizono et al., "Liquid-liquid extraction of transition metal ions with an alkylhistidine extractant", Separation and Purification Technology, vol. 80 No. 2, Elsevier B.V., Jul. 29, 2011, p. 390-395.

International Search Report for PCT/US2013/062480 dated Jul. 18, 2013.

Office Action dated Aug. 31, 2015 in Chinese Application No. 201380042794.1.

* cited by examiner

INDIUM EXTRACTION AGENT AND INDIUM EXTRACTION METHOD

CROSS-REFERENCE TO RELATED APPLICATIONS

This application is the national phase under 35 U.S.C. §371 of PCT International Application No. PCT/JP2013/062480, filed Apr. 26, 2013, which claims the benefit of Japanese Application No. 2012-181884, filed Aug. 20, 2012, the entire contents of the aforementioned applications are hereby incorporated herein by reference.

TECHNICAL FIELD

The present invention relates to an indium extraction agent and an indium extraction method, more particularly, an extraction agent and an extraction method, which efficiently isolate and extract indium from an acidic solution containing indium and zinc.

BACKGROUND ART

Indium is supplied in the form of alloy targets with zinc and tin and paste as a material for transparent conductive films such as a semiconductor device and a touch panel and is widely used.

Ores incidentally contain indium in a very slight amount and also indium is unevenly distributed. So it is not easy to ensure a stable supply of indium. In addition, ores containing indium contain lead and zinc in a grossly excessive amount as compared to the amount of indium in many cases. Thus, when recovering indium there is a great problem with efficiently separating indium from lead and zinc.

Therefore, indium is obtained from ores, and furthermore indium is also obtained by recovering electronic circuit boards discarded in the city, defective items produced in production processes and other target materials which have been effectively finished and the like and recycling these. When the discarded electronic circuit boards and the like are recycled to obtain indium, however, there is still a problem with efficiently separating indium from lead and zinc.

As a method for separating indium from lead and zinc, a solution obtained by a two-stage neutralization treatment during the zinc leaching residue treatment step of zinc smelting is used as a solution to be extraction containing gallium and indium, and this solution to be extraction is adjusted to pH 2.4 to 3.6. Separately, a chelating agent is added to an organic solvent, and an extraction organic solvent having an organic phase in which a part of the protons in this chelating agent is substituted by an alkaline earth metal is also prepared. It is proposed that both these solutions be mixed to extract and isolate gallium and indium in the above solution to be extracted (see Patent Document 1). The method described in Patent Document 1, however, cannot be directly applied to a solution leached using an acid, for example, a low pH solution with as pH less than 2, and costs for as neutralizer to adjust pH, neutralization equipment, and much time for treatment are required.

It is also suggested that indium, gallium and zinc are each isolated using a chelating extraction agent having phosphinic acid as a ligand (see Patent Document 2). The invention described in Patent Document 2, however, has high selectivity to zinc in coexistence with cadmium. Accordingly, when it is required to separate indium from zinc out of members not using cadmium like modern electronic members, it cannot be said that indium is efficiently obtained.

Patent Document 1: Japanese Unexamined Patent Application, Publication No. 2000-212658
Patent Document 2: Japanese Unexamined Patent Application, Publication No. 2009-256291

DISCLOSURE OF THE INVENTION

Problems to be Solved by the Invention

An object of the present invention is to provide an extraction agent and an extraction method which selectively extract and, at a low cost, recover indium from an acidic solution containing indium and zinc.

As a result of repeated intensive research to solve the above problems, the present inventors found that the above object could be achieved by providing an indium extraction agent comprising an amide derivative represented by the following general formula (I), thereby completing the present invention.

Means for Solving the Problems

Specifically, the following are provided in the present invention.

(1) The present invention is an indium extraction agent comprising an amide derivative represented by the following general formula (I):

(wherein $R^1$ and $R^2$ each represents the same or different alkyl group,
the alkyl group may be a straight chain or a branched chain,
$R^3$ represents a hydrogen atom or an alkyl group, and
$R^4$ represents a hydrogen atom or any group other than an amino group which is bound to the α carbon as an amino acid).

(2) In addition, the present invention is the indium extraction agent according to (1), wherein the amide derivative is any one or more of a glycine amide derivative, a histidine amide derivative, a lysine amide derivative, an aspartic acid amide derivative and a normal-methylglycine derivative.

(3) In addition, the present invention is an indium extraction method, wherein indium is extracted from an acidic solution by solvent extraction by an indium extraction agent according to (1) or (2).

(4) In addition, the present invention is the indium extraction method according to (3), wherein the amide derivative is a glycine amide derivative and the acidic solution is subjected to the solvent extraction with the pH of the acidic solution adjusted to a range of between 1 or more to 3.7 or less.

(5) In addition, the present invention is the indium extraction method according to (3), wherein the amide derivative is a histidine amide derivative and the acidic solution is subjected to the solvent extraction with the pH of the acidic solution adjusted to a range of between 1 or more to 3.6 or less.

(6) In addition, the present invention is the indium extraction method according to (3), wherein the amide derivative is a normal-methylglycine derivative and the acidic solution is subjected to the solvent extraction with the pH of the acidic solution adjusted to a range of between 0.7 or more to 3.4 or less.

(7) In addition, the present invention is an indium extraction method according to any of (3) to (6), wherein, an acidic solution with a pH of 0.6 or less is mixed with the extraction agent which has extracted the indium from the acidic solution to carry out back extraction, and, thereafter, the extraction agent and the acidic solution are separated to obtain the acidic solution containing the indium.

(8) In addition, the present invention is the indium extraction method according to (7), wherein, an acidic solution with a pH of between 1.8 or more and 2.2 or less and an extraction agent are mixed with the extraction agent which has extracted the indium from the acidic solution, and the extraction agent and the acidic solution are then separated to remove zinc from the extraction agent and the back extraction is then carried out.

(9) In addition, the present invention is an indium extraction method according to any of (3) to (8), wherein the acidic solution containing indium and zinc is a solution obtained by mixing sulfuric acid with a member containing indium and zinc and not containing cadmium and leaching indium and zinc from the member.

Effects of the Invention

According to the present invention, unlike conventional extraction agents, indium can be efficiently isolated from an acidic solution containing zinc at a high concentration even in the low pH region. In addition, the number of extraction steps can be decreased in actual operation and the equipment size can be compressed, and thus indium can be recovered at a low cost.

PREFERRED MODE FOR CARRYING OUT THE INVENTION

Specific embodiments of the present invention will be now described in detail. It is noted, however, that the present invention is not limited to the following embodiments, and can be properly changed within the scope of the object of the present invention and carried out.

Extraction Agent

The extraction agent used for indium extraction comprises an amide derivative represented by the following general formula (I).

In the formula, the substituents $R^1$ and $R^2$ each represent the same or different alkyl group. The alkyl group may be a straight chain or a branched chain. $R^3$ represents a hydrogen atom or an alkyl group. $R^4$ represents a hydrogen atom or any group other than an amino group which is bound to the α carbon as an amino acid. In the present invention, lipophilicity is enhanced by introducing an alkyl group into the amide skeleton and the present invention can be used as an extraction agent.

The above amide derivative is any one or more of a glycine amide derivative, a histidine amide derivative, a lysine amide derivative, an aspartic acid amide derivative and a normal-methylglycine derivative (also referred to as a sarcosine amide derivative).

When the amide derivative is a glycine amide derivative, the above glycine amide derivative can be synthesized by the following method. First, a 2-halogenated acetyl halide is added to an alkyl amine having a structure represented by NHR$^1$R$^2$ (R$^1$ and R$^2$ are the same as the above substituents R$^1$ and R$^2$) and the hydrogen atom of the amine is substituted with a 2-halogenated acetyl by a nucleophilic substitution reaction to obtain a 2-halogenated (N,N-di)alkylacetamide.

Next, the above 2-halogenated (N,N-di)alkylacetamide is added to a glycine or N-alkyl glycine derivative, and one hydrogen atom of the glycine or N-alkyl glycine derivative is substituted with a (N,N-di)alkylacetamide group by a nucleophilic substitution reaction. With the two-step reaction, a glycine alkyl amide derivative can be synthesized.

It is noted that by replacing glycine with histidine, lysine, aspartic acid or normal-methylglycine, a histidine amide derivative, a lysine amide derivative, an aspartic acid amide derivative or a normal-methylglycine derivative can be synthesized.

Extraction of Indium

To extract indium ions using an extraction agent synthesized by the above method, the pH of an acidic aqueous solution containing indium ions is adjusted and then the acidic solution is added to an organic solution having the above extraction agent as a component, and mixed. Therefore, an objective valuable metal ion can be selectively extracted in the organic phase. It is noted that by adjusting the above extraction agent to an appropriate concentration using a known diluent and the like as required, isolation ability can be improved and operation can be stabilized.

After the extraction of indium ions, an acidic solution adjusted to a lower pH than that of the above acidic aqueous solution is added to the organic solvent as a back extraction starting solution and stirred to isolate an objective indium ion by extraction to the organic solvent. Furthermore, by the back extraction of the objective indium ion from the organic solvent, the objective indium ion can be recovered in the aqueous solution. For example, an aqueous solution in which nitric acid, hydrochloric acid or sulfuric acid is diluted is suitably used as the back extraction solution. In addition, indium ions can be also concentrated by properly changing the ratio of organic phase and aqueous phase.

The organic solvent can be any solvent in which an extraction agent and metal extraction species are dissolved, and examples thereof include chlorine solvents such as chloroform and dichloromethane, aromatic hydrocarbons such as benzene, toluene and xylene, aliphatic hydrocarbons such as hexane, and the like. These organic solvents may be used alone or two or more solvents may be used in combination. Alcohols such as 1-octanol may be mixed.

The concentration of the extraction agent can be properly set depending on the concentration of indium. In addition, the stirring time and extraction temperature may be properly set depending on the conditions of the acidic aqueous solution of indium ions and the organic solution of the extraction agent.

To efficiently recover indium from an acidic aqueous solution containing indium and zinc, by adding an alkali, an acid or the like to the acidic aqueous solution containing indium and zinc, the acidic aqueous solution may be adjusted within the pH range in which indium is extracted and the extraction of zinc is inhibited.

When extraction is carried out in the pH region in which the extraction rate of indium is low, the amount of indium extracted, i.e., the recovery rate declines.

Contrarily, when extraction is carried out in the pH region in which the extraction rate is excessively high, zinc is also extracted and thus the purity of indium recovered is decreased.

Multistep extraction is therefore industrially carried out in many cases. Indiscriminately increasing the number of extraction steps, however, is not preferred in terms of equipment investment and costs. Like the present invention, in particular, in the field which tries to isolate indium from scrap and ores and the like, it is thought that extraction with 3 or 4 or less steps at the most is practical in terms of the liquid volume to be treated and the like. Because of this, the extraction rate of indium in one step extraction is preferably 50% or more, more preferably 80% or more and even more preferably 95% or more. Contrarily, the extraction rate of zinc, which is an impurity, is preferably 20% or less and more preferably 10% or less.

The basic structure of the extraction agents used in the present invention is the same, but the small difference in optimum pH region is caused by a small difference in structure, and the agents can be properly used depending on the target liquids and conditions.

When the extraction agent is a glycine amide derivative, for example, the pH is preferably adjusted to between 0.7 or more and 3.7 or less and more preferably adjusted to between 1.1 or more and 2.2 or less.

In addition, when the extraction agent is a histidine amide derivative, the pH is preferably adjusted to between 0.7 or more and 3.6 or less and more preferably adjusted to between 1.3 or more and 2.2 or less.

In addition, when the extraction agent is a normal-methylglycine derivative, the pH is preferably adjusted to between 0.7 or more and 3.4 or less and more preferably adjusted to between 1.4 or more and 2.2 or less.

By bringing an organic solution after extraction, with which indium has been extracted, into contact with an acidic solution having a lower pH than that of the original acidic solution as a back extraction starting solution, incidentally, indium in an extraction agent is distributed into the back extraction starting solution to recover indium, and simultaneously the extraction agent can be regenerated. The pH of the back extraction starting solution is preferably low in the respect in which indium can be recovered with high efficiency, but when the pH is too low, the recovery rate is not improved to more than a certain level and costs also increase. Further, when the pH is too low, there are problems in that, for example, the decomposition of an extraction agent is promoted. Therefore, the pH is preferably in the range of between 0.4 or more to 0.8 or less.

In addition, before the above back extraction of an extraction agent which has extracted indium, the extraction agent is brought into contact with an acidic solution for washing (also referred to as scrubbing), thereby being able to isolate a part of extracted zinc from the extraction agent. Consequently, the purity of indium obtained by back extraction can be improved. The pH of the acidic solution added in the washing step is preferably in a range of between 1.8 or more to 2.2 or less with respect to which the extraction rate of indium is 95% or more and the extraction rate of zinc is almost 0%.

EXAMPLES

The present invention will be now described in more detail by way of examples thereof. It is noted, however, that the present invention is not limited to these descriptions.

Synthetic Example 1

Synthesis of Extraction Agent Comprising Glycine Amide Derivative

As an example of amide derivatives forming an extraction agent, a glycine amide derivative represented by the following general formula (III) was synthesized, that is, N-[N,N-bis (2-ethylhexyl)aminocarbonylmethyl]glycine (or also referred to as N,N-di(2-ethylhexyl)acetamide-2-glycine, hereinafter referred to as "D2EHAG") into which two 2-ethylhexyl groups were introduced.

D2EHAG was synthesized as follows. First, as shown in the following reaction formula (II), 23.1 g (0.1 mol) of commercially available di(2-ethylhexyl)amine and 10.1 g (0.1 mol) of triethylamine were taken and chloroform was added thereto and dissolved. Next, 13.5 g (0.12 mol) of 2-chloroacetyl chloride was added dropwise thereto and the obtained mixture was washed once with 1 mol/l hydrochloric acid and then washed with ion exchanged water, and the chloroform phase was separated.

Next, anhydrous sodium sulfate was added thereto in an appropriate amount (approximately 10 to 20 g) for dehydration, followed by filtration to obtain 29.1 g of yellow liquid. The structure of this yellow liquid (reaction product) was identified using a nuclear magnetic resonance analyzer (NMR) and the above yellow liquid was confirmed to have the structure of 2-chloro-N,N-di(2-ethylhexyl)acetamide (hereinafter, referred to as "CDEHAA"). It is noted that the yield of CDEHAA was 90% with respect to di(2-ethylhexyl)amine, which is a raw material.

(II)

CDEHAA

Next, as shown in the following reaction formula (III), 8.0 g (0.2 mol) of sodium hydroxide was dissolved by adding methanol, and 15.01 g (0.2 mol) of glycine were also added thereto. While stirring the obtained solution, 12.72 g (0.04 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Figure 1:
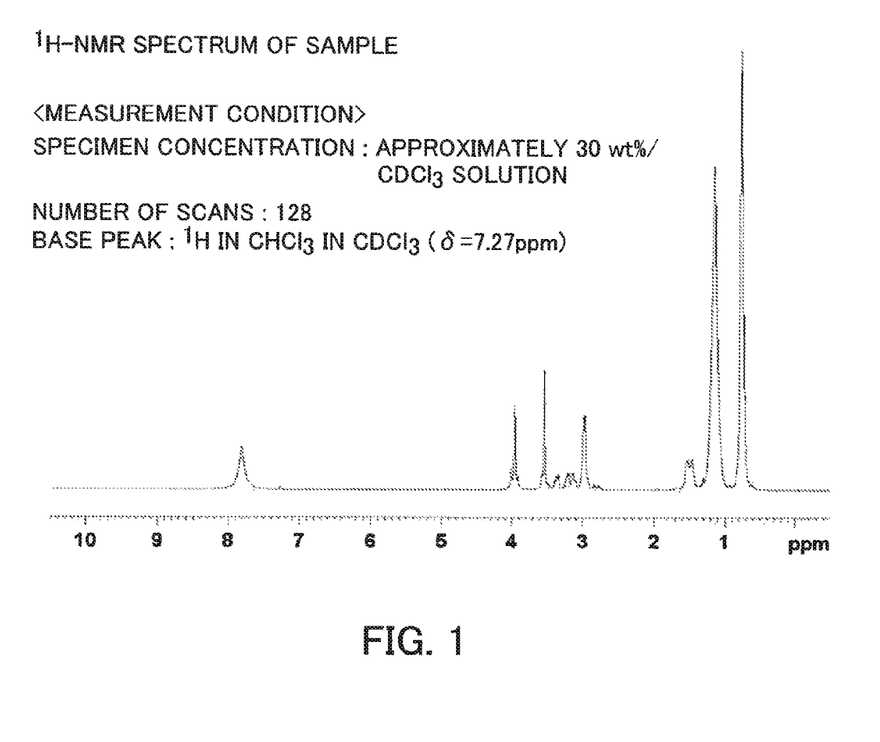
FIG. 1 is a diagram showing the $^{1}$H-NMR spectrum of a glycine amide derivative involved in Synthetic Example 1.
Figure 2:
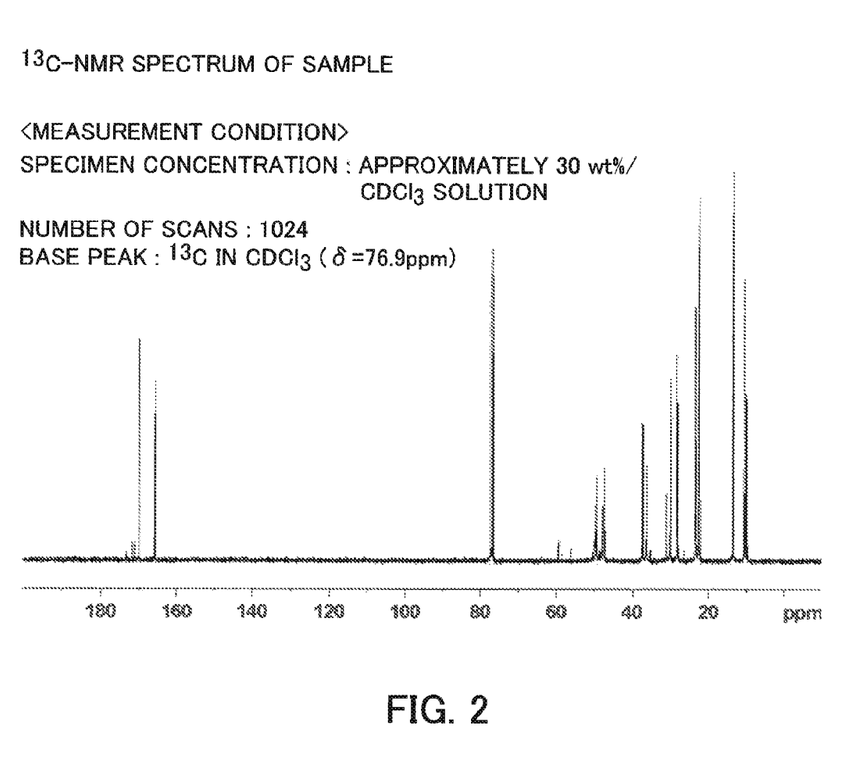
FIG. 2 is a diagram showing the $^{13}$C-NMR spectrum of a glycine amide derivative involved in Synthetic Example 1.

Anhydrous magnesium sulfate was added to this chloroform phase in an appropriate amount for dehydration, followed by filtration. The solvent was removed under reduced pressure again to obtain 12.5 g of yellow paste. The yield was 87% based on the amount of the above CDEHAA. The structure of the yellow paste was identified by NMR and elemental analysis and the yellow paste was confirmed to have the structure of D2EHAG as shown in FIG. 1 and FIG. 2. The extraction agent in Synthetic Example 1 was obtained by undergoing the above steps.

Synthetic Example 2

Synthesis of Extraction Agent Comprising Histidine Amide Derivative

As another example of amide derivatives forming an extraction agent, a histidine amide derivative represented by the following general formula (IV) was synthesized, that is, N-[N,N-bis(2-ethylhexyl)aminocarbonylmethyl]histidine (or also referred to as N,N-di(2-ethylhexyl)acetamide-2-histidine, hereinafter referred to as "D2EHAH") into which two 2-ethylhexyl groups were introduced.

D2EHAS was synthesized as follows. As shown in the following reaction formula (IV), 5.3 g (0.132 mol) of sodium hydroxide were dissolved by adding methanol, and 11.8 g (0.132 mol) of sarcosine (N-methylglycine) were also added thereto. While stirring the obtained solution, 36.3 g (0.12 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Anhydrous magnesium sulfate was added to this chloroform phase in an appropriate amount for dehydration, followed by filtration. The solvent was removed under reduced pressure again to obtain 26.8 g of yellowish brown paste. The yield was 60% based on the amount of the above CDEHAA. The structure of the yellow paste was identified by NMR and elemental analysis and the yellow paste was confirmed to have the structure of D2EHAS. The extraction agent in Synthetic Example 2 was obtained by undergoing the above steps.

Synthetic Example 3

Synthesis of Extraction Agent Comprising Normal-Methylglycine Derivative As another example of amide derivatives forming an extraction agent, a normal-methylglycine derivative represented by the following general formula (I) was synthesized, that is, N-[N,N-bis(2-ethylhexyl)aminocarbonylmethyl]sarcocine (or also referred to as N,N-di(2-ethylhexyl)acetamide-2-sarcocine, hereinafter referred to as "D2EHAS") into which two 2-ethylhexyl groups were introduced.

D2EHAH was synthesized as follows. As shown in the following reaction formula (V), 16 g (0.4 mol) of sodium hydroxide were dissolved by adding methanol, and 31.0 g (0.2 mol) of histidine were also added thereto. While stirring the obtained solution, 13.2 g (0.04 mol) of the above CDEHAA were slowly added dropwise thereto. After completion of dropwise addition, the solution was stirred with alkaline conditions maintained. After completion of stirring, the solvent in the reaction liquid was distilled off and the residue was dissolved by adding ethyl acetate. This solution was washed and the ethyl acetate phase was separated.

Anhydrous magnesium sulfate was added to this ethyl acetate phase in an appropriate amount for dehydration, followed by filtration. The solvent was removed under reduced pressure again to obtain 9.9 g of yellowish brown paste. The yield was 57% based on the amount of the above CDEHAA. The structure of the yellowish brown paste was identified by NMR and elemental analysis and the yellowish brown paste was confirmed to have the structure of D2EHAH. The extraction agent in Synthetic Example 3 was obtained by undergoing the above steps.

Extraction of Indium

Using the extraction agents in Synthetic Examples 1 to 3, indium was extracted and isolated.

Example 1

An original liquid containing 8 mg/l indium and 5 mg/l zinc was divided into 3 ml portions, and sulfuric acid was added to these to adjust the pH to from 0.8 to 3.7. The several types of sulfuric acidic solution and an n-dodecane solution with the same volume as above (3 ml) having the extraction agent involved in Synthetic Example 1 at a concentration of 0.01 mol/l were added to test tubes. The test tubes were put into a thermostatic chamber at 25° C. and shaken. At this time, the pH of the sulfuric acid solutions was adjusted using 0.1 mol/l nitric acid, ammonium nitrate and ammonia.

Figure 3:
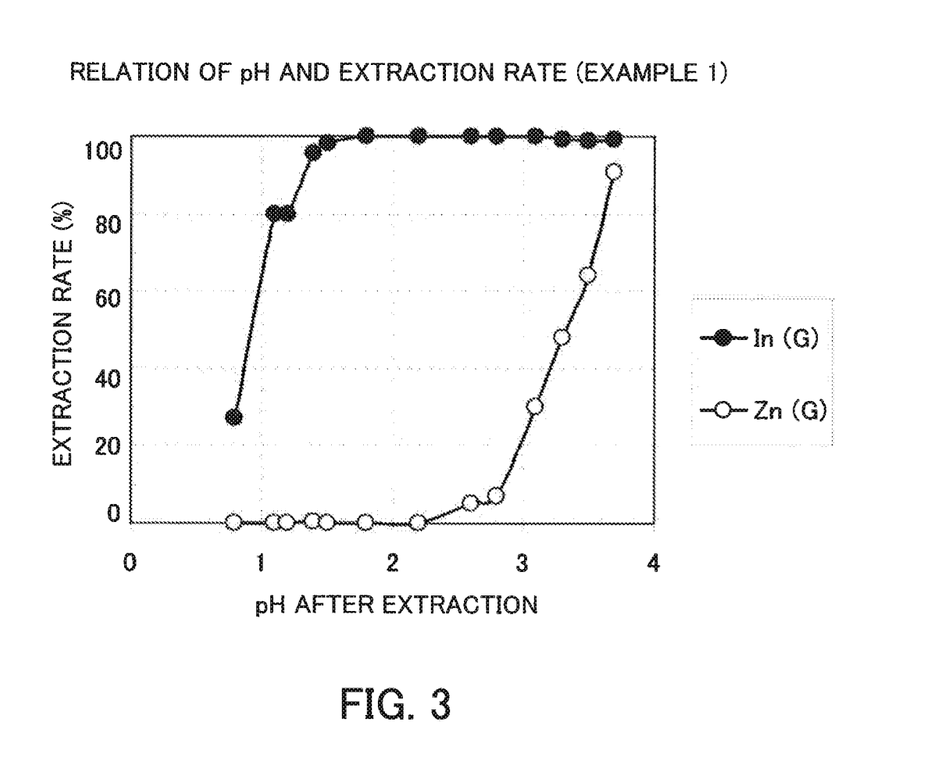
FIG. 3 shows the results when indium was extracted from an acidic solution containing indium and zinc using an extraction agent comprising a glycine amide derivative.

After shaking, the aqueous phase was separated and the concentration of indium and the concentration of zinc were measured using an inductively coupled plasma-atomic emission spectrophotometer (ICP-AES). In addition, the organic phase was subjected to back extraction using 2 mol/l nitric acid. The concentration of indium and the concentration of zinc in the back extraction phase were measured using ICP-AES. Using these measurement results, the extraction rates of indium and zinc were defined by the amount of material in the organic phase/(the amount of material in the organic phase+ the amount of material in the aqueous phase) and obtained. The results are shown in FIG. 3. In FIG. 3, the abscissa is the pH of sulfuric acidic solution and the ordinate is the extraction rate of indium or zinc (unit: %). In the graph, a closed circle indicates the extraction rate of indium and an open circle indicates the extraction rate of zinc.

Example 2

Figure 4:
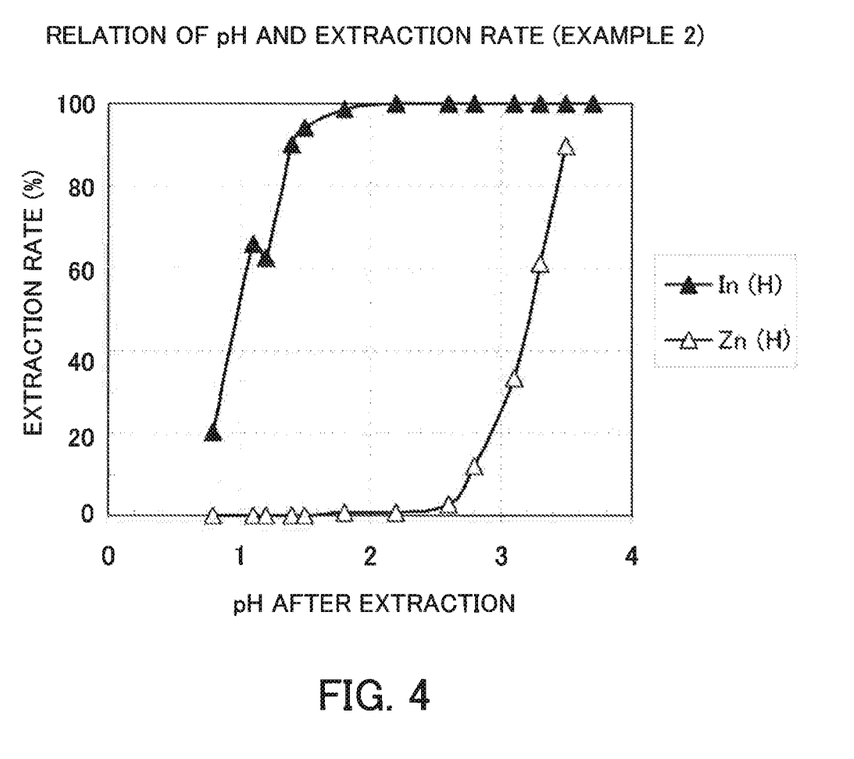
FIG. 4 shows the results when indium was extracted from an acidic solution containing indium and zinc using an extraction agent comprising a histidine amide derivative.

Indium was extracted from a sulfuric acidic solution containing indium and zinc in the same method as in Example 1 except that the extraction agent involved in Synthetic Example 2 was used as the extraction agent in place of the extraction agent involved in Synthetic Example 1. The results are shown in FIG. 4. In FIG. 4, the abscissa is the pH of sulfuric acidic solution and the ordinate is the extraction rate of indium or zinc (unit: %). In the graph, a closed triangle indicates the extraction rate of indium and an open triangle indicates the extraction rate of zinc.

Example 3

Figure 5:
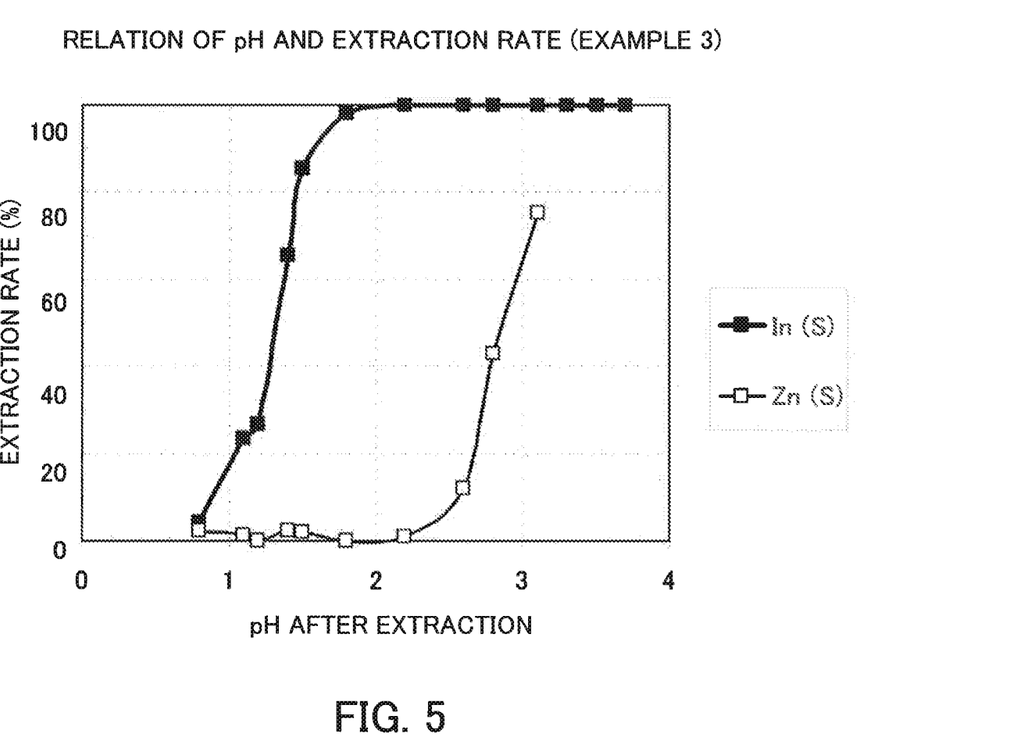
FIG. 5 shows the results when indium was extracted from an acidic solution containing indium and zinc using an extraction agent comprising a normal-methylglycine derivative.

Indium was extracted from a sulfuric acidic solution containing indium and zinc in the same method as in Example 1 except that the extraction agent involved in Synthetic Example 3 was used as the extraction agent in place of the extraction agent involved in Synthetic Example 1. The results are shown in FIG. 5. In FIG. 5, the abscissa is the pH of sulfuric acidic solution and the ordinate is the extraction rate of indium or zinc (unit: %). In the graph, a closed square indicates the extraction rate of indium and an open square indicates the extraction rate of zinc.

Figure 6:
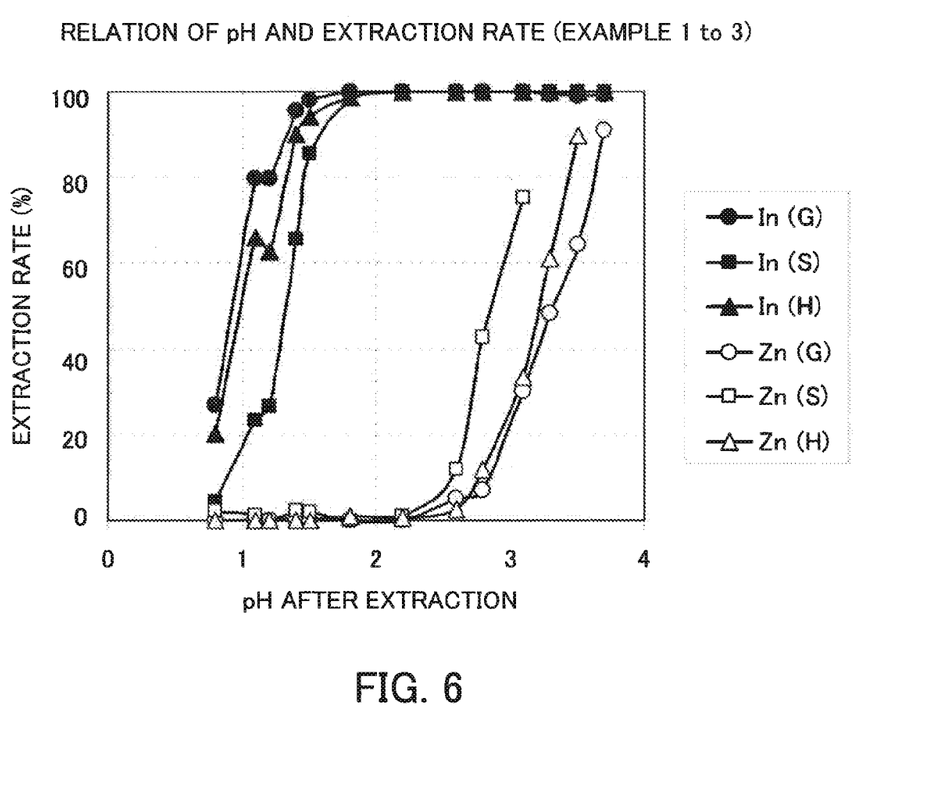
FIG. 6 is a diagram summarizing the results shown in FIG. 3 to FIG. 5 in a graph.

It was verified that indium could be efficiently extracted from a sulfuric acidic solution containing indium and zinc using the extraction agents in Synthetic Examples 1 to 3 (FIG. 3 to FIG. 5). It was also verified that the influence on the application range depending on each type of extraction agent was small and zinc and indium could be easily isolated around the vicinity of pH 2 as shown in FIG. 6. Furthermore, extraction agents using amino acids having a lysine amide derivative and an aspartic acid amide derivative as a main component can be considered. The extraction behaviors of these agents are the same as when using the extraction agents involved in Synthetic Examples 1 to 3 in view of complex stability constants thereof. Therefore, it is inferred that indium can be efficiently isolated.

The invention claimed is:

1. An indium extraction method, wherein indium is extracted from a first acidic solution comprising indium by solvent extraction using an indium extraction agent comprising an amide derivative represented by the following general formula (I):

wherein, $R^1$ and $R^2$ each represent the same or different alkyl group,
the alkyl group is optionally a straight chain or a branched chain,
$R^3$ represents a hydrogen atom or an alkyl group, and
$R^4$ represents a hydrogen atom or any group other than an amino group which is bound to the α carbon as an amino acid.

2. The indium extraction method according to claim 1,
wherein the amide derivative is the glycine amide derivative, and
the first acidic solution is subjected to the solvent extraction with the pH of the first acidic solution adjusted to a range of between 1 to 3.7.

3. The indium extraction method according to claim 2, wherein a second acidic solution with a pH of 0.6 or less is mixed with the extraction agent which has extracted the indium from the first acidic solution, and, thereafter, the extraction agent and a third acidic solution containing the indium are separated.

4. The indium extraction method according to claim 2, wherein the first acidic solution comprises indium and zinc, and the first acidic solution is a solution obtained by mixing sulfuric acid with a member containing indium and zinc and not containing cadmium and leaching indium and zinc from the member.

5. The indium extraction method according to claim 1,
wherein the amide derivative is the histidine amide derivative, and
the first acidic solution is subjected to the solvent extraction with the pH of the first acidic solution adjusted to a range of between 1 to 3.6.

6. The indium extraction method according to claim 5, wherein a second acidic solution with a pH of 0.6 or less is mixed with the extraction agent which has extracted the indium from the first acidic solution, and, thereafter, the extraction agent and a third acidic solution containing the indium are separated.

7. The indium extraction method according to claim 5, wherein the first acidic solution comprises indium and zinc, and the first acidic solution is a solution obtained by mixing sulfuric acid with a member containing indium and zinc and not containing cadmium and leaching indium and zinc from the member.

8. The indium extraction method according to claim 1,
wherein the amide derivative is the normal-methylglycine derivative, and
the first acidic solution is subjected to the solvent extraction with the pH of the first acidic solution adjusted to a range of between 0.7 to 3.4.

9. The indium extraction method according to claim 8, wherein a second acidic solution with a pH of 0.6 or less is mixed with the extraction agent which has extracted the indium from the first acidic solution, and, thereafter, the extraction agent and a third acidic solution containing the indium are separated.

10. The indium extraction method according to claim 8, wherein the first acidic solution comprises indium and zinc, and the first acidic solution is a solution obtained by mixing sulfuric acid with a member containing indium and zinc and not containing cadmium and leaching indium and zinc from the member.

11. The indium extraction method according to claim 1, wherein a second acidic solution with a pH of 0.6 or less is mixed with the extraction agent which has extracted the indium from the first acidic solution, and, thereafter, the extraction agent and a third acidic solution containing the indium are separated.

12. The indium extraction method according to claim 11, wherein a fourth acidic solution with a pH of 1.8 and 2.2 and an extraction agent are mixed with the extraction agent which has extracted the indium from the first acidic solution, and the extraction agent and the fourth acidic solution are then separated to remove zinc from the extraction agent and the back extraction is then carried out.

13. The indium extraction method according to claim 12, wherein the first acidic solution comprises indium and zinc, and the first acidic solution is a solution obtained by mixing sulfuric acid with a member containing indium and zinc and not containing cadmium and leaching indium and zinc from the member.

14. The indium extraction method according to claim 11, wherein the first acidic solution comprises indium and zinc, and the first acidic solution is a solution obtained by mixing sulfuric acid with a member containing indium and zinc and not containing cadmium and leaching indium and zinc from the member.

15. The indium extraction method according to claim 1, wherein the first acidic solution comprises indium and zinc, and the first acidic solution is a solution obtained by mixing sulfuric acid with a member containing indium and zinc and not containing cadmium and leaching indium and zinc from the member.

16. The indium extraction method according to claim 1, wherein the amide derivative is any one or more of a glycine amide derivative, a histidine amide derivative, a lysine amide derivative, an aspartic acid amide derivative and a normal-methylglycine derivative.

* * * * *